(12) United States Patent
Lynn

(10) Patent No.: US 7,654,996 B2
(45) Date of Patent: *Feb. 2, 2010

(54) CATHETER FLUSHING FLUID LOCK SYSTEM AND METHOD

(76) Inventor: Lawrence Allan Lynn, 862 Curley Ct., Columbus, OH (US) 43235

( * ) Notice: Subject to any disclaimer, the term of this patent is extended or adjusted under 35 U.S.C. 154(b) by 0 days.

This patent is subject to a terminal disclaimer.

(21) Appl. No.: 10/533,749

(22) PCT Filed: Nov. 4, 2002

(86) PCT No.: PCT/US02/35163

§ 371 (c)(1), (2), (4) Date: May 10, 2005

(87) PCT Pub. No.: WO2004/041343

PCT Pub. Date: May 21, 2004

(65) Prior Publication Data

US 2006/0015074 A1 Jan. 19, 2006

(51) Int. Cl.
*A61M 31/00* (2006.01)

(52) U.S. Cl. .................. 604/506; 604/34; 604/250; 604/537

(58) Field of Classification Search ................ 604/500, 604/506–508, 523, 533, 537, 245, 246, 250, 604/256, 264, 266, 267, 178, 30, 33, 34; 251/4, 7, 9, 10

See application file for complete search history.

(56) References Cited

U.S. PATENT DOCUMENTS

| 4,235,412 | A | * | 11/1980 | Rath et al. ................... 251/10 |
| 5,035,399 | A | * | 7/1991 | Rantanen-Lee .............. 251/10 |
| 5,318,546 | A | * | 6/1994 | Bierman ..................... 604/250 |
| 5,738,657 | A | | 4/1998 | Bryant et al. |
| 6,592,558 | B2 | * | 7/2003 | Quah ......................... 604/250 |
| 6,689,109 | B2 | * | 2/2004 | Lynn ......................... 604/250 |
| 6,958,049 | B1 | * | 10/2005 | Ash ............................. 604/28 |

* cited by examiner

Primary Examiner—Kevin C Sirmons
Assistant Examiner—Bhisma Mehta

(57) ABSTRACT

A catheter-flushing extension tube for maintaining the patency and sterility of the lumen of an indwelling catheter. The system is comprised of an extension tube in fluid connection with an indwelling catheter; the extension tube defines an internal volume and at least one sealed proximal terminal for intermittent connection with an external fluid source. The extension tube is configured such that the internal volume of the tube can be progressively reduced at a plurality of different times so that the extension tube itself provides the source of catheter flush solution for intermittently flushing the catheter.

7 Claims, 5 Drawing Sheets

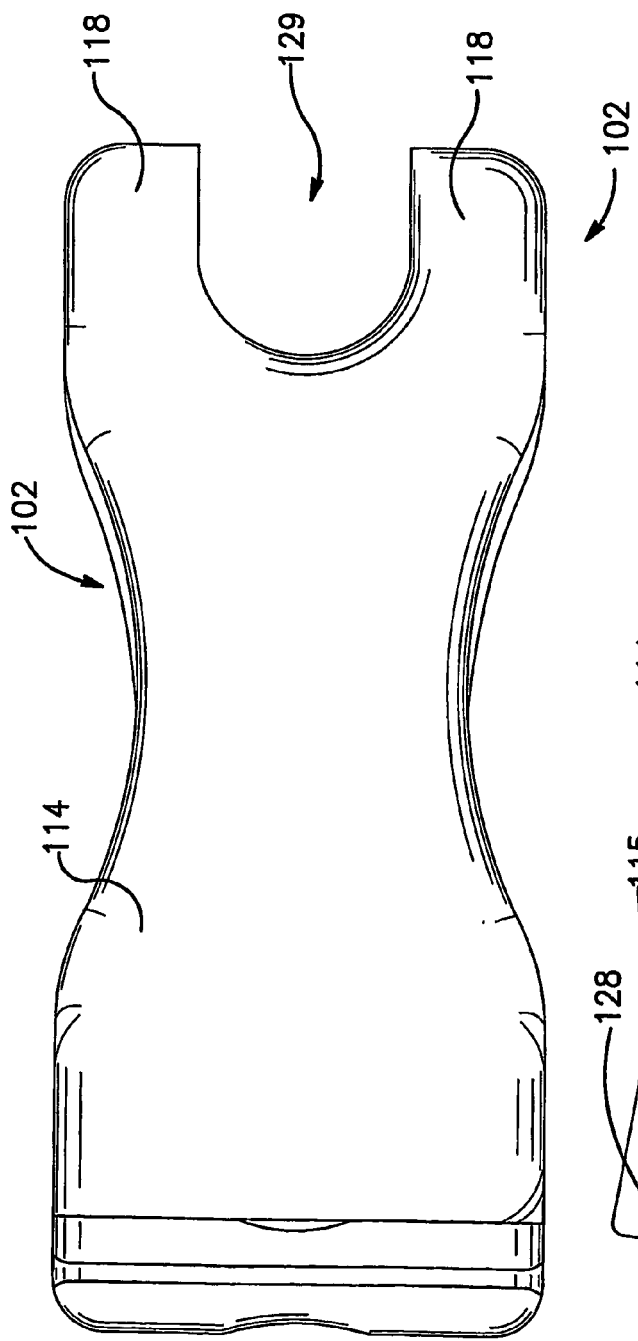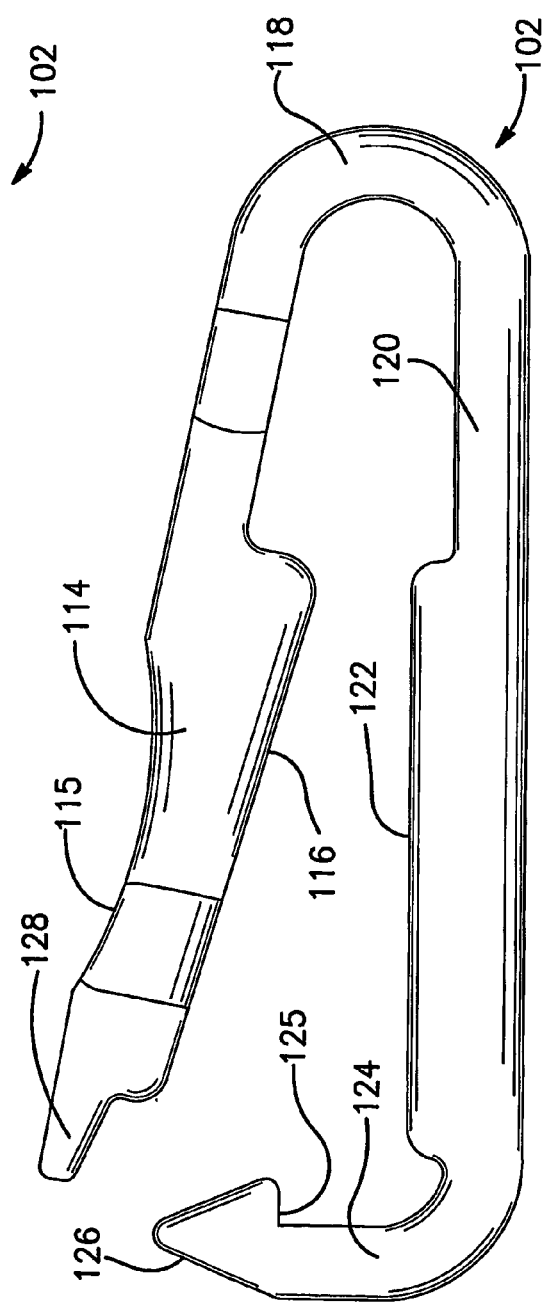

CATHETER FLUSHING FLUID LOCK SYSTEM AND METHOD

RELATED APPLICATIONS

This application is a 371 application serial number PCT/US02/35163, filed Nov. 4, 2002.

FIELD OF THE INVENTION

This invention relates to fluid lock systems for indwelling catheters and to flushing procedures, solutions, and methods for maintaining the patency of fluid locked systems.

BACKGROUND AND SUMMARY OF THE INVENTION

Intravenous catheters represent the most common parenteral site for medication delivery. A large portion of these catheters, placed in either a peripheral or central vein, are left in situ for extended periods of time. Commonly these catheters are connected with tubing systems having closed sealed ends. These tubing systems are filled with a flush solution, which is injected through a seal or valve at a proximal terminal of the system. The act of injecting and filling with solution, a blind ended tube in fluid connection with a blood vessel has been termed a "lock procedure" because it sets up, in fluid connection with flowing blood, a simple and relatively static, vacuum-locked column of solution, extending from the solution-blood interface to a sealed proximal terminal. Within a resting fluid locked system, the pressure is relatively uniform and is substantially equal to the pressure of the flowing blood. The fluid lock system generally has a relatively fixed volume and limited elasticity so that variations in pressure within the flowing blood cannot cause substantial net or reciprocating flow of fluid between the locked system and the blood vessel. Although the term "heparin lock" or "saline lock" has been widely used, alternative flush solutions may be used. For this reason the term "fluid lock" or "lock" is preferred to designate such a procedure and/or system (which includes or is otherwise connectable to a catheter).

The use of a fluid lock system to maintain catheter patency has many advantages over other systems such as conventional pump based or gravity feeding flow system. Most of these systems maintain patency by maintaining a slightly greater pressure within the system than in the flowing blood. For many clinical situations, application of the simple lock system is preferred because it is considerably less expensive than these alternative systems. Lock systems are also associated with greater patient mobility, less complexity, and less fluid administration. However, despite its simplicity the lock procedure remains associated with considerable expense and substantial work for the nurses administrating and maintaining fluid lock systems. In addition the lock procedure has, since its inception more than 15 years ago, been associated with an unacceptable failure rate, which contributes generally to the expense of the procedure.

Other than leakage, the most important modes of failures of a conventional lock system are either thrombotic, infectious, or a combination of both. The rate of thrombotic failure has been reported to exceed 10%. One of the factors precipitating failure is reflux of blood into the tip of the catheter lumen associated with an inadvertent internal volume reduction of the fluid lock. Today the proximal seals of fluid locked systems are most commonly luer receiving valves or cannula receiving septae. As is standard with the lock procedure, these terminals generally automatically seal upon withdrawal of the cannula or luer after a flush maneuver, however, with many such systems, such withdrawal can result in removal of a small volume of fluid from the locked fluid column causing reflux of blood into the catheter lumen to accommodate that volume loss. U.S. patent application Publication No. 20010039403 published Nov. 8, 2001, of the present inventor, (the entire contents of which is incorporated by reference as if completely disclosed herein) discloses a positive flow generator for flushing indwelling fluid lock medical systems and for displacing such refluxed blood back out of the catheter tip.

Another factor precipitating failure of a fluid lock is the common state of facilitated diffusion, which develops at the leading edge of the locked fluid. Over time, diffusion, facilitated by the minor pressure variations in venous blood at the catheter lumen-to-blood interface causes blood components to gradually invade the distal end of the lumen of a fluid locked catheter. This process also induces migration of flush solution constituents from the lock, such as the anticoagulant or antimicrobial and this can contribute to failure. Peripheral catheters, being protected from central pressure variations by distance and venous valves, are exposed to much less pressure variation than central catheters and these catheters are commonly filled with saline alone. However, some blood still slowly penetrates the lumen at the tip of these catheters. For this reason it is common hospital protocol to flush such peripheral catheters every eight hours or so, to displace the small volume of blood, which enters the tip (if no scheduled infusion of medication has been provided during that interval which would otherwise achieve that goal).

To flush the lock system and its fluid connected catheter lumen, sterile saline or other flush solution is commonly aspirated from a multi-dose vial. Since, at the present time, most drug vials have elastomeric septae intended for receiving a sharp needle, this aspiration procedure often requires a disposable adapter to prevent needle sticks, which adds to the general cost of the lock procedure. A simple saline flush also requires a sterile syringe and with some systems, a sterile cannula connected with the syringe, each further adding to the expense. Because multi-dose vials carry the risk of cross contamination if not managed properly and because time dependent personnel costs are progressively rising in hospitals, an alternative, pre-filled disposable saline flush syringes are being offered by corporations. However the storage of sterile flush solution within individually packaged syringes is also expensive, and such devices can cost in excess of $0.50 for a single unit. There are hundreds of millions of such procedures performed in the US each year so that, considering all related costs, the expense of maintaining locks in the US alone probably exceeds several hundreds of millions of dollars.

In addition to the expense, each time the lock system is reentered the infection risk is increased to the patient because the outside instrument (such as a cannula, luer, or needle) can carry bacteria and yeast into the lock where they can proliferate and induce bacteremia and/or fungemia which are associated with considerable expense and can be fatal). In the 21st century many more patients have been subjected to transplantation or otherwise have reduced immune systems making it more important to reduce routine entry of external devices into lock systems as much as possible. The catheter hub and internal lumen, have long posed an important infection risk problem for patients at home or in hospitals and the contamination risk is directly related to the number of entries into the system. Because each occurrence is associated with some risk, procedures associated with repetitive reentry (as with periodic flushing) are important access mechanism for microbial invaders. Considered collectively, throughout the United States, each year there are a vast number of such entries into lock systems for the purpose of flushing alone, for this reason, although the infectious risk of each flush maneuver is low, the number of patients who die each year due to a contamination during a routine flush, although difficult to measure, is probably quite high. In addition, although each event is again associated with a low occupational risk, the nurse remains potentially exposed to infectious material, and potentially infectious waste is generated, anytime a disposable device such as a cannula enters a tubing system connected to a patient's vascular system.

Central catheters are exposed to substantially greater pressure variations, and are often left in for many weeks, and pose an increased risk in the event of lock entry related colonization. Furthermore, the state of facilitated diffusion is heightened with these catheters and thrombus formation can readily occur, causing catheter occlusion and, at times, dangerous thrombus propagation. This is especially true in patients with malignancy, which often produces a state of hyper coagulation. Clot formation can also contribute to catheter related infection and bacteremia. The extent of facilitated diffusion, combined and potential, for relative states of thrombophilia in patients with combined morbidities, produces an environment wherein optimal prevention of occlusion and infection of central catheters requires meticulous and expensive catheter maintenance.

To prevent these important causes of mortality and morbidity, new catheter flush mixtures such as combinations of antimicrobial and anticoagulants have been developed.

The rational for, as well as disclosure of, a kit for the delivery of such a combination is disclosed in U.S. Pat. No. 6,187,768 (the disclosure of which is incorporated by reference as if entirely disclosed herein). This patent provides additional background for the present invention.

However well formulated these new flush solutions are vulnerable to dilution as a function of facilitated diffusion within the lumen of the catheter adjacent the solution-blood interface. This can cause a loss in efficacy if locked dwell times are extended between flushes. However as can readily be seen by understanding the "kit" disclosed in the aforementioned patent, despite short-term efficacy, each of these newer locking procedures can require considerable effort and expense. Many central catheters, especially multilumen catheters, have at least one lumen, which is idle for extended periods but which still requires frequent locking procedures unassociated with medication infusion. Also many patients receive intermittent therapy (such as chemotherapy) but have long term indwelling lines for many weeks or months. In these patients flushing may represent the only access related infectious risk to the interior of the lock over a large percentage of the catheter dwell time.

The present inventor recognized that one important fundamental problem with conventional locked systems is that; the actions taken toward achieving the goal of prevention of infection and those toward the goal of prevention of thrombosis are potentially competitive. Frequent entry into the proximal terminal to provide flushing to prevent thrombosis can induce infection whereas; minimization of entry to reduce the risk of infection can induce thrombosis. The present inventor recognized that, it would be preferable, toward the goal of minimizing both risks, to develop a lock system, which could be entered once and flushed many times. Further is was recognized by the present inventor that the efficacy of specialized lock formulations such as, BDTA-antimicrobial combinations, would be enhanced, without the need for additional entry into the locked system and with minimal administration of these formulations to the patient, if these formulations could be stored in a lock system and intermittently advanced forward in small increments to replace lost constituents at the solution-to-blood interface.

According to one aspect of the invention a system is provided including a specialized flush solution formulation containing a beneficial agent, such as an antimicrobial and/or anticoagulant, and a reservoir fluid-locked with a catheter for storing the formulation, the reservoir defines an internal space filled with the formulation in fluid communication with a blood vessel through a lumen within the catheter. The space has an internal pressure essentially equal to the pressure within the blood vessel, such that the formulation within the lumen interfaces with blood within the blood vessel at a relatively static formulation-to-blood interface adjacent the distal end of the lumen. The system includes a volume reducer for engaging the reservoir and for reducing the volume of the formulation contained within the space by facilitating the movement of at least a portion of the formulation into the interface to increase the concentration of the formulation along the interface, the volume reducer preferably includes an element for reducing the volume of the reservoir by predetermined discrete and limited increments at a plurality of different times to increase the efficacy of the formulation with a minimum of transfer of the formulation into the patients blood vessel.

According to one presently preferred embodiment the present invention, a closed system, such as a fluid locked tubing system, is provided with at least one sealed proximal terminal, which can be a luer receiving valve or cannula receiving septum. The closed system is connectable with, or integral with, at least a portion of an indwelling catheter residing beneath a patient's skin and/or vein. The closed system defines an internal volume and is at least partially filled with flush after a flush maneuver through is injected through at least one proximal terminal by an external flush system such as a syringe. A residual flush volume of flush solution, such a mixture of antimicrobial and anticoagulant (as described in U.S. Pat. No. 6,187,678), remains within the tubing system after a flush maneuver and the aforementioned internal volume defines this residual flush volume. This volume of fluid, in its locked state after the flush maneuver has been completed and enough time has passed for equalization, has generally an equal pressure to the pressure of the blood at the blood-to-flush solution interface of the locked system. According to one aspect of the present invention, the pressure of the residual flush solution is intermittently increased and the fluid advanced by intermittent and progressive reduction of the internal volume of the system. The reduction of the internal volume is preferably achieved by a volume reduction system comprising a volume reducer, which displaces the volume from a more proximal position toward a more distal position so that residual fluid is displaced toward the blood-to-flush solution interface of the catheter lumen. The volume reduction system can be a single reducer, which provides multiple levels of reduction, and which is intermittently activated to achieve progressively a greater level reduction of internal volume. Alternatively, the volume reduction system can be comprised of a plurality of multiple elements such as a plurality of small clamps, such as pinch clamps with elongated or flattened compressing surfaces, for compressing and thereby reducing the volume of the tube. These elements can be separate and slidable so that they can be conveniently positioned on the tube, depending on tape down considerations, or they can be integral or otherwise connected or connectable to the tube. Alternatively selectable volume reducing elements can be provided as connected or connectable to either or both of the proximal or distal terminals or can be integral with, and/or comprise a portion of the proximal and or distal terminal. As another alternative according to the present invention multiple elements such as clamps may be molded together as a single piece connected by a flexible elongated living hinge for mounting with an extension tubing set so that the tubing remains flexible when the connected elements are mounted with it. The elements are preferably either injection molded separately or together using a suitable medical grade polymer such as polypropylene or nylon, alternatively for greater clarity and to enhance its appearance the elements may be molded of polycarbonate or a polycarbonate-polyester blend may be used. The living hinge can be of the type described in U.S. Pat. No. 5,514,117, which is assigned to the present inventor (the entire contents of which is incorporated by reference as if completely disclosed herein) and marketed by Abbott laboratories under the trade name Lifeshield Connector. The tube is preferably flexible and is preferably comprised of a medical grade polymer, which has known compatibility with medication. For example a short segment of conventional intravenous tubing in wide use as extension sets is suitable for this purpose; however tubing molded with enlarged regions for compression can also be used to reduce the length of the clamps or increase the volume of the displaced flush solution.

One preferred catheter-flushing system for intermittently flushing the lumen of an indwelling catheter, wherein the catheter has an indwelling portion beneath the skin of a patient, includes a patient mounted tubing system in fluid connection with the indwelling portion. The tubing system defines an internal volume and at least one proximal terminal for intermittent connection with an external fluid source. The proximal terminal includes a seal for promptly sealing upon disconnection of the fluid source from the terminal. At least a portion of the flush solution entering the tubing system through the terminal remains sealed within the tubing system after the fluid source has been disconnected from the system, thereby defining a residual volume of flush solution within the tubing system. The system also includes a volume reducer, which is configured to induce a reduction in the volume of flush solution within the lock system. In the presently preferred embodiment the reducer is configured for progressively reducing the internal volume of the tubing system at a plurality of different times to displace a plurality of fractions of the residual volume into the indwelling portion of the catheter to intermittently flush the indwelling portion with the flush solution. The activation of the volume reducer preferably and/or its elements reduces the volume within the tubing system by at least one discrete volume. Preferably a plurality of activations of the volume reducer, and/or its elements, reduces the volume within the tubing system by a plurality of discrete volumes at a plurality of different times to provide intermittent flushing of the said catheter portion over a prolonged time interval. The flush solution is preferably saline or a mixture of diluent and at least one of an anticoagulant and an antimicrobial agent. These flush solutions are "stored" in the lock system. In the presently preferred embodiment these flush solutions are stored within the tubing system of the locked system, and are intermittently propelled forward as in discrete boluses to enhance the antimicrobial and anticoagulant efficacy of the solutions within the catheter-flushing system and to mitigate the influence of time dependent dilution adjacent the flush fluid-blood interface. If preferred the sequence can be automated such that the reducer reduces the volume at pre-selected intervals.

While the application of a volume reducer, which progressively reduces the internal volume of the lock, is presently preferred, in another embodiment the reducer achieves a net reduction of flush solution without a permanent change in internal volume of the lock system. This embodiment includes a diffusion facilitator, such as a separate alternating pressure generating element such as a vibratory element or sound emitter for alternating the pressure within the lock to facilitate the movement of flush solution within the lock system and preferably within a fluid reservoir comprising a proximal portion lock system. With this embodiment the adverse effects of facilitated diffusion induced by pressure variations within the distal blood vessel are offset by the intermittent provision of pressure variations within the proximal lock to move flush solution and any associated anticoagulant forward in the lock and thereby achieve dilution of the invading blood components at the tip of the catheter lumen which effectively dilutes the components of the clotting cascade preventing thrombosis. With such a system, while blood components slowly enter the system, rather than summarily flush them out in discrete volume reduction maneuvers, their potential to induce thrombus is mitigated by the intermittent facilitated movement of a higher concentration of flush solution with or without anticoagulant and antimicrobial components toward the distal end of the catheter lumen.

In one embodiment the system includes a single tube for mounting with a patient, the tube has a distal end connectable to the catheter and at least one proximal end with a terminal for intermittent connection with a source of flush solution. The terminal includes a seal for sealing the proximal end of the tube when the source of flush solution is disconnected from the terminal. The tube further defines an internal open space defining an internal volume which is reducible, and a lumen extending through from the sealed proximal terminal to the distal end, so that when a source of flush solution is connected to the terminal, flush solution can enter the tube from the fluid source through the terminal and flow through the lumen to at least partially fill the internal space. The lumen defines at least a portion of the internal volume. The system further includes a volume reducer comprised of at least one volume-reducing element. The volume reducer is sized and configured to sequentially reduce the internal volume of the tube at a plurality of different times after the distal end has been connected with the catheter, the flush solution has been flowed into the space from the source, and the source has been disconnected from the terminal. In one embodiment the tube is elongated and has different diameters along its length.

One preferred method for intermittently flushing the lumen of an indwelling catheter, wherein the catheter has a indwelling portion beneath the skin of a patient, comprises the steps of:

Disposing a patient mounted tubing system in fluid connection with the indwelling portion of the catheter, wherein the system has at least one proximal terminal. The tubing system defines an internal space, defining an internal volume.

Flowing flush solution from an external fluid source, through at least one terminal and through the said tubing system into the indwelling portion, with at least a portion of the solution at least partially filling the internal space.

Then promptly sealing the proximal terminal of the tubing system such that at least a portion of the flush solution remains sealed within the tubing system thereby defining a residual volume of flush solution within the tubing system, the fluid being locked in fluid connection with the blood vessel.

Then, at a plurality of different times, increasing the pressure within the tubing system, as by progressively, and in discrete steps, reducing the internal volume of the tubing system, to displace a plurality of fractions of the residual volume into the indwelling portion to intermittently flush the indwelling catheter portion with the flush solution.

The reducer and or one of its elements can be a tube compressing member configured for compressing the tubing system to a plurality of sequentially lower levels of internal volume, such that each time the system volume is reduced further, an additional portion of the stored residual volume of flush solution is displaced toward the blood-flush solution interface to displace blood which may have invaded the catheter or otherwise diluted or diminished the effect of the antimicrobial or anticoagulant.

In the case of a central catheter this residual flush solution can represent the expensive mixture of saline and an anticoagulant with or without an antimicrobial. In the peripheral catheter this is commonly saline alone. However, in either case the present inventor recognized that the presence of the residual fluid could be exploited to enhance the maintenance of patency of indwelling catheters and to prevent the need for frequent outside flushes of the system. The present inventor recognized that a system could be constructed which provided intermittent flushes from the residual fluid contained within a closed tubing system connected with a catheter thereby reducing cost, nurse exposure and work time, and catheter contamination risk. Upon the realization, the present inventor developed a sequential catheter flush generation system, which retains the advantages of simplicity and convenience of a basic lock system, but which provides for activation of a sequence of small discrete displacement volumes to be delivered at selected intervals from the locked system to maintain catheter patency without the need to open or enter the system.

Another aspect of the present invention comprises a system for maintaining the patency and sterility of the lumen of a catheter system within a blood vessel, the blood vessel containing flowing blood. The lumen defines a distal end within the blood vessel. The system contains a flush solution mixture of a diluent, such as saline, and at least one of an antimicrobial and anticoagulant stored in a fluid locked reservoir, such as a tubing system, in fluid communication with a blood vessel through a lumen, the reservoir has an internal pressure essentially equal to the pressure within the blood vessel and the flush solution within the reservoir interfaces with blood within the blood vessel at a solution-to-blood interface adjacent the distal end of the lumen. The system includes a volume reducer for periodically reducing the volume of the reservoir to advance the mixture toward the interface to flush blood components from the lumen and to increase the concentration of the mixture adjacent the interface, to thereby increase the efficacy of the mixture with a minimum of delivery of the mixture into the patient's vascular system.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 2 shows a top view of a catheter-flushing clamp;

FIG. 3 shows a side view of the catheter-flushing clamp of FIG. 2;

DETAILED DESCRIPTION OF THE PRESENTLY PREFERRED EMBODIMENTS

Figure 1:
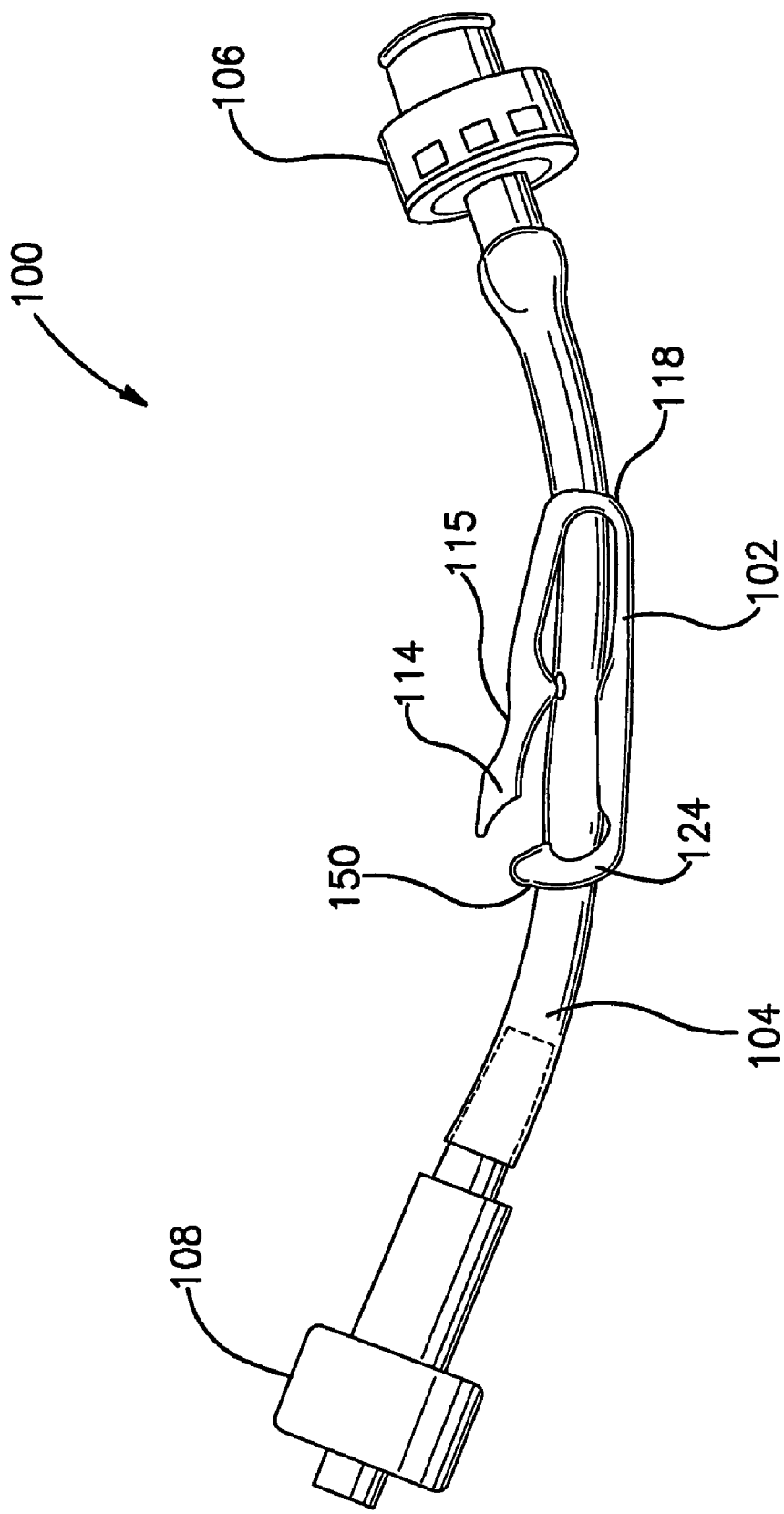
FIG. 1 shows one presently preferred embodiment of a non-sequential catheter-flushing fluid lock system according to the present invention.

As shown in FIG. 1 a catheter flush generation system 100 includes a one piece, locking catheter-flushing clamp 102 (of the type disclosed in the aforementioned patent application of the present inventor) mounted upon an intravenous extension tube 104 having a closed proximal terminal 106, which as shown, is preferably a luer receiving valve integral with tubing 104 (as, for example, bonded and/or swayed onto tubing 104). Although a luer receiver is shown the proximal terminal 106 can be another closed hub such as an elastomeric hub for receiving a blunt cannula such as the hub marketed under the trade names Interlink and Lifeshield marketed by Baxter and Abbott Laboratories respectfully. The system 100 further includes a conventional distal luer lock connector 108 for engaging the hub of a catheter.

Figure 4:
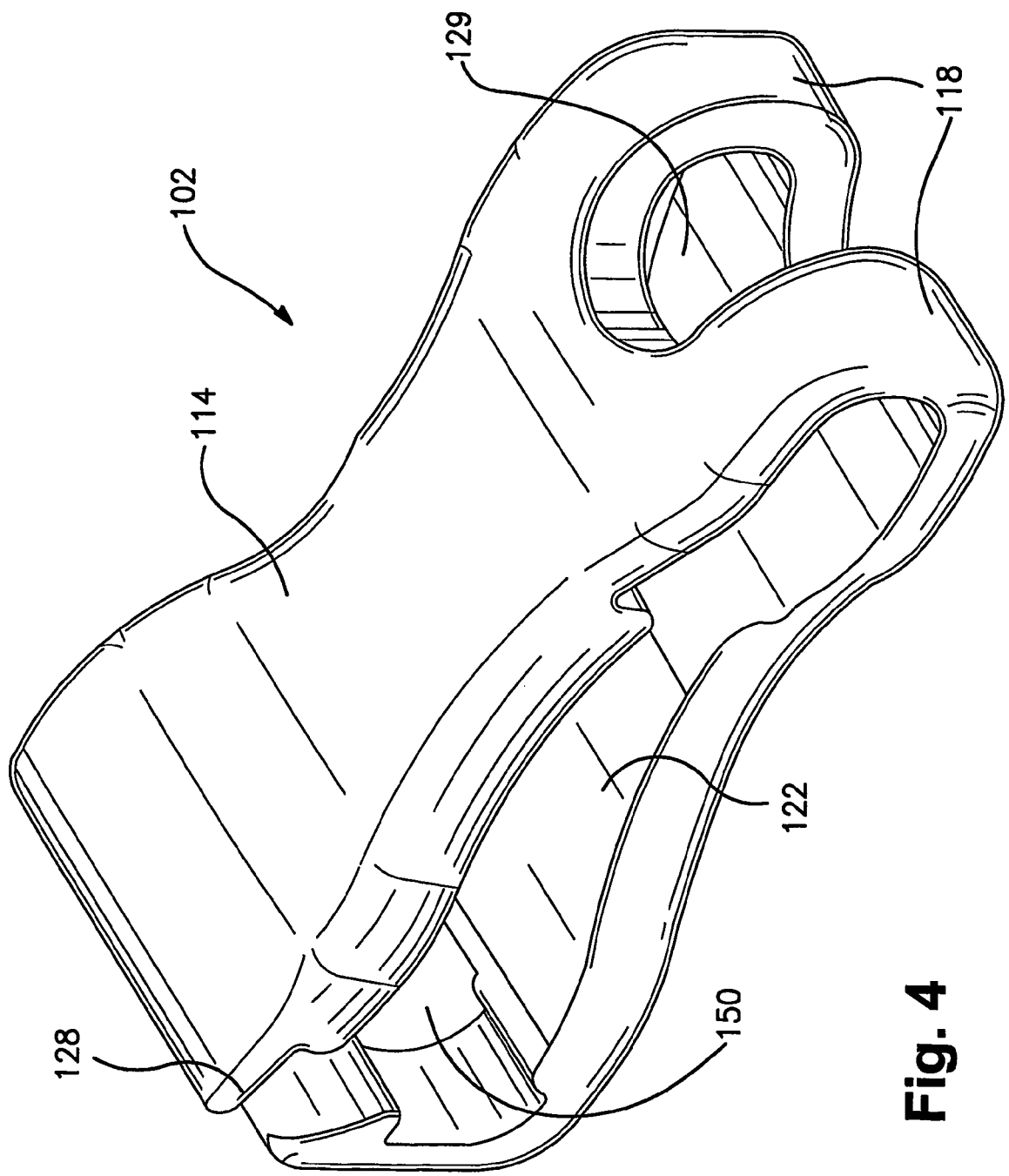
FIG. 4 shows a perspective view of the catheter-flushing clamp of FIG. 2.

As shown in FIGS. 2-4, the catheter-flushing clamp 102 has a locking arm 114, with an top surface 115 for application of thumb pressure and an elongated, upper compression surface 116 and a pair of proximal curved hinges 118 connecting the locking arm 114 to a base 120 which projects under and opposes the locking arm 114. The base 120 includes an elongated, lower compression surface 122. The base 120 also includes a distal flexible post 124, which provides a latch 125 for detachably capturing the distal end 128 of the locking arm 114 when the locking arm 114 is deflected toward the base 120 and under the latch 125. (Basic flexible post-arm latching mechanisms are well known in the art and are in wide use with the conventional pincer clamps for central venous catheters used for dialysis.) The post 124 includes a bevel 126 facing distally so that inadvertent disconnection is minimized (as by contact pressure against the outer surface of the post 124). Such a distal orientation of the bevel 126 can direct contact force against the bevel toward the locking arm 114 rather than away from it. Alternatively the post 124 can be angled inwardly toward the locking arm 114 (for example 10-20 degrees from vertical) to direct such a force toward the locking arm 114.

The hinges 118 include a passage 129 for tubing 104. Tubing 104 projects within clamp 102 between upper compressing surface 116 and the lower compressing surface 122. (If preferred, especially when a very small diameter tube 104 is provided, a segment of tubing 104, which extends between these surfaces, can have an enlarged internal diameter so that the displaced volume generated by the catheter flush generation system 100 is increased. Tubing 104 extends distally out the clamp 102 through distal passage 150 (FIG. 4).

A smaller and more lightweight flush system is preferred. Although other sizes may be used, the presently preferred length of the tubing 104 is between about 5 and 20 cm. The tube can have a wall thickness of about 0.4-0.5 mm and an internal diameter ranging from of about 1 mm-2 mm (for micro bore tubing) to about 2 mm-10 mm (as for flush systems for use when higher flush volumes are preferred). The clamp can have a length 15 to 30 mm. And a compression length of about 5-15 mm depending of the volume of the displacement desired and internal volume of the tubing.

Figure 5:
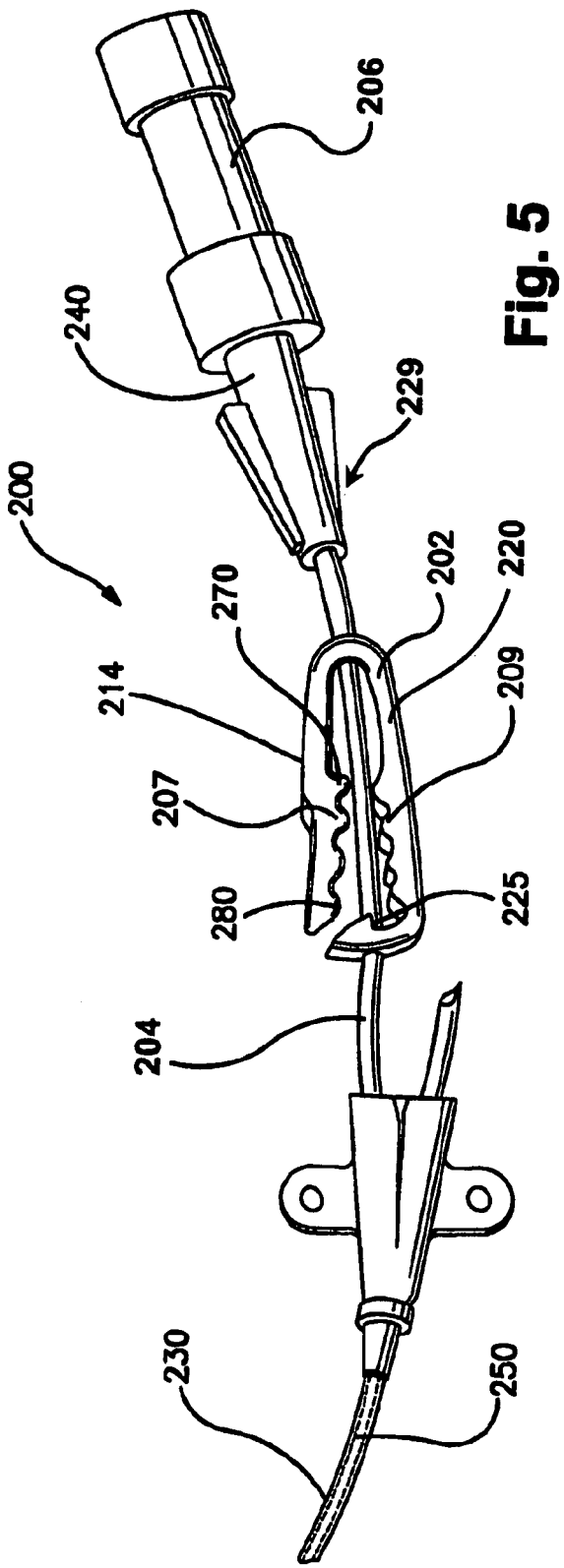
FIG. 5 shows another presently preferred embodiment of a non-sequential catheter-flushing fluid lock system according to the present invention.

FIG. 5 shows another catheter flush generation system 200 with catheter-flushing clamp 202 with a plurality of opposing compression elevations 207 and 209 on upper arm 214 and base 220 mounted on one of the pigtail 229 of a closed double lumen peripherally inserted central catheter (PICC catheter) 230. A conventional closed proximal hub is shown threaded onto the PICC catheter hub 240 sealing the proximal end of the system 200. This figure illustrates the very small diameter of the two lumens 250 extending through this catheter 230 into which the fluid is displaced by the closure of the catheter-flushing clamp 202.

Figure 6:
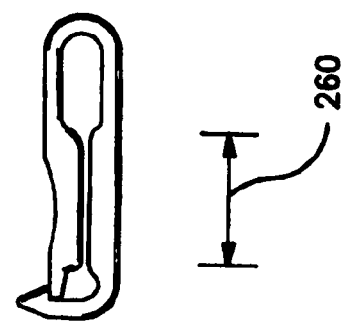
FIG. 6 shows a side view of the catheter-flushing clamp in the closed position.

FIG. 6 shows an embodiment of a catheter-flushing clamp in its closed position. This figure illustrates that, according to the present invention, the displacement volume of the catheter flush generation system 100 and 200 are set by the compressed length 260 and the diameter of the segment of the tubing 104 or 204 along the compressed length 260. (If compression elevations are provided as in FIG. 5 some fluid may be trapped between these elevations so that the compression length 260 can be slightly increased.) According to the present invention, the internal diameter of the tubing 104 and the compressed length 260 are selected to achieve the desired range of volumes of displaced catheter flushing fluid.

In operation, first the catheter flush generation system 200 and catheter 230 have been filled with fluid injected through the distal terminal 206. Then the locking arm 214 is deflected downward into a closed position compressing tubing 204 between compressing surfaces and the locking arm in the locked position under the latch 225. As shown in FIG. 5, the proximal portion of the compressing surface can have a projecting member 270, which, during closure, promptly occludes the proximal portion of tubing 204 thereby propelling the fluid volume within tube 204 distally toward the catheter as the arm 214 is further deflected into the locked position. The compressing surface can be flat or (as shown in FIG. 6) can be comprised of sequential elevations (as in FIG. 5), or it can be convex or concave longitudinally. Once the clamp has been latched, according to the preferred embodiment of the present invention, additional force applied to achieve additional compression of the clamp will not further displace additional fluid so that rebound of fluid back into the catheter does not occur when the thumb pressure is released. In some embodiments (as in FIG. 6), when the arm is held in position by the latch, a uniform distance is provided between the distal face of the upper compressive surface and opposing lower surface, matched to the width of the tube when the tube has a completely compressed lumen, so that, when force applied to the top of the clamp is released after latching, complete compression of the lumen is maintained such that the lumen does not enlarge to induce negative pressure causing reflux of fluid back toward the clamp. If preferred, greater flexibility in the distance between compressing surfaces can be provided by providing a distal elevation 280 (FIG. 5) at the distal end of one or both of the compressing surfaces to assure compression is complete.

Figure 7:
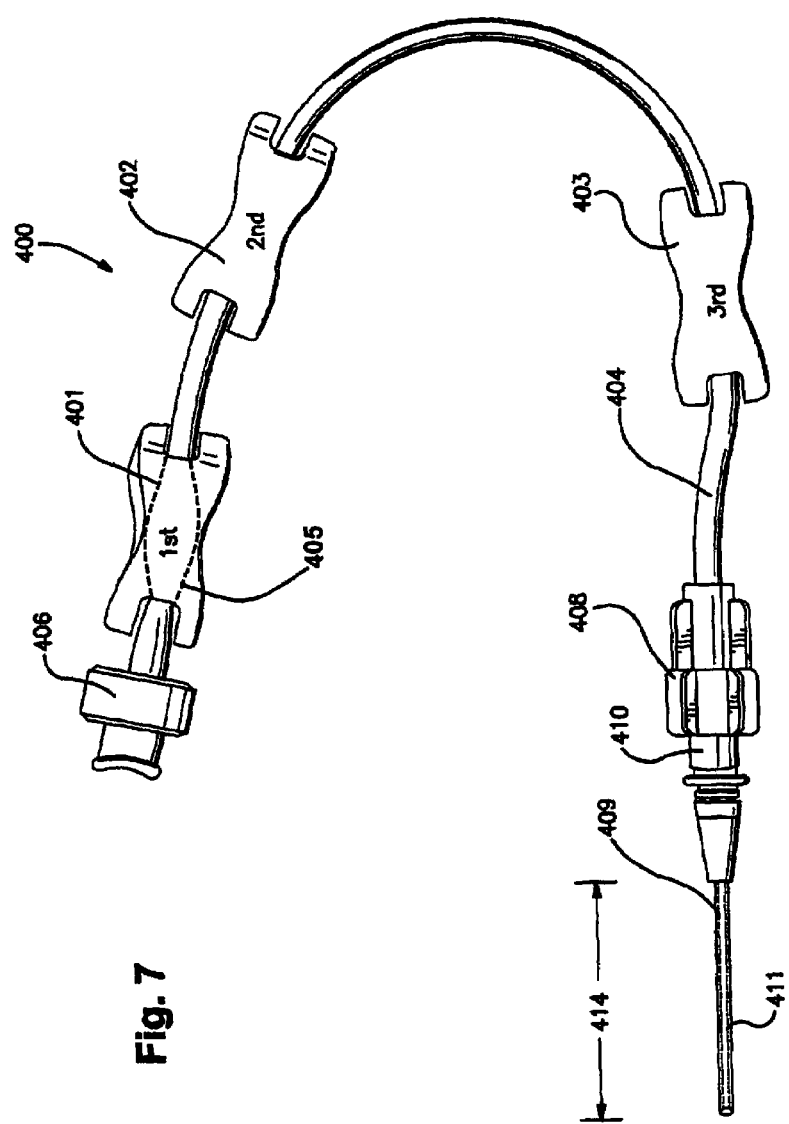
FIG. 7 shows one presently preferred embodiment of a sequential catheter-flushing fluid lock system according to the present invention.

A presently preferred embodiment of the sequential catheter-flushing fluid lock system according to the present invention, which can substantially reduce the need to routinely access fluid lock systems, is shown in FIG. 7. Three low profile, catheter-flushing clamps 401, 402, and 403 are mounted in a series upon tubing 404. Tubing 404 has enlarged portion 405 and closed proximal terminal 406 (shown as a luer receiving valve) and a distal luer terminal 108, for connection with a catheter 409 at catheter hub 410. The catheter 409 has an internal lumen 411 defining a length shown as 414. These catheter-flushing clamps 401, 402 and 403 are marked at both the top (thumb contact) surface 115 and the bottom surface with "1st, 2nd, and 3rd" to remind the nurse of the order of closure every 8 hours as will be discussed. The tubing 404 preferably has a generous internal diameter (for example in the range of 4-6 mm) so that the flush volume generated by each catheter-flushing clamp is relatively high in comparison to the volume of the lumen 411 along length 414. In one example, a catheter-flushing clamp of the type for example shown in FIGS. 2-4 with a compression length of 9 mm mounted on tubing with a internal diameter of about 3.5-4 mm, can generate a flush volume exceeding the entire internal volume of the potential indwelling length 414 of a typical 1.5 inch 18 gauge catheter (as for example the "Insyte" catheter marketed by Becton Dickinson), so that the sequential closure of each of the three such flushing clamps 401,402,403, can achieve complete flushing of the lumen 411 of catheter 409 on three separate occasions without requiring the opening or internal access of the system 400. Yet the volume of the flush is low, predetermined, and discrete so as to minimize the amount of flush solution displaced into the patient's systemic system.

In operation of the sequential catheter flush system 400; the nurse connects the system to catheter hub 410 (if it is not pre-connected or integral with the catheter). The nurse then flushes ("charges") the system. If the proximal terminal is not a positive pressure valve or if the valve is simply threaded rather than permanently attached, the first (most proximal) clamp 401 is closed. After this, if no medication has been infused in the interim, each sequential clamp (402 then 403) is closed at 8 hr. intervals to flush the catheter 409 every shift (this interval may be prolonged with specialized formulations as discussed previously). After 24 hours, or eight hours after the last catheter-flushing clamp has been closed, all the catheter-flushing clamps are opened and the system 400 is "recharged" by flushing the system 400 with saline through the proximal terminal 406. The system 400 is now ready to provide another 24 hours of sequential catheter flush. Accordingly one method for intermittently flushing the catheter comprises steps of reducing the internal volume of the extension tube after a first interval, a second interval, and a third interval where the first residual volume is less than initial volume, the second residual volume is less than the first residual volume. The method can maintain the catheter for 24 hrs and can be repeated for another 24 hours.

When this new method is applied to maintain patency of an indwelling catheter, external flushing need only be applied every 24 hours or even less frequently, greatly reducing cost and the number of times the system is opened and potentially reducing the infection risk. Deployment of the sequential catheter flush system could, over several years; save a hospital hundreds of thousands of dollars while at the same time reducing nurse workload and patient and nurse infection risk. In many cases the patient may be receiving medication (such as an antibiotic) only every 24 hours, or the protocol (such as may be applied with PICC catheters) may call for flushing only every 12 to 24 hours so that the sequential reducing of volume every 24 hours up to 3 times can provide a method for maintaining the patency of an indwelling catheter over a 24-72 hour period. For these reasons, the sequential catheter flush system according to the present invention can with some patients, eliminate all flushes other than those delivered immediately after antibiotic infusion. Failure rates of lock devices due to delayed or missed flushes may also be minimized by the present invention since the sequential catheter flush system is more easily applied and less time consuming.

If desired to make the sequential catheter flush generation system less obtrusive the catheter-flushing clamps can be reduced in length and the internal diameter of the tubing increased along the segment to be compressed so the combined length of the multiple clamps is reduced. Alternatively, by enlarging the internal tubing diameter and/or the compression length much larger volumes can be generated so that the system can be applied to large volume central lines such as dialysis catheters. According to another aspect of the invention, the method of closed lock-based catheter flushing can be taught to patients enhancing the safety of home infusion and reduce the need for nursing visits.

In another alternative embodiment the lock-based catheter flush generation system can be provided with catheter flushing clamp having a plurality of with levels of closure (as achieved for example with multiple latches) and a large diameter-tubing segment between the compressing surfaces so that sequential closure at each level can be provided selectively at intervals to provide sequential discrete flushes. In a further embodiment, two catheter flushing clamps are provided combined with a positive displacement valve (such as the valve marketed under the trade name Posiflow marketed by Becton Dickinson) provided as a permanent (non-threaded) proximal terminal. Since the valve is a positive displacement device and it is secured permanently to the tube so that the patient need not have back up for disconnection protection, closure of the first clamp after accessing the valve is not required; therefore, only two catheter-flushing clamps need be mounted to tube to provide 24 hours of catheter maintenance.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for intermittently flushing the lumen of an indwelling catheter with fluid comprising flush solution derived from an external fluid source when the catheter is no longer in fluid communication with the external fluid source, the catheter lumen having an indwelling portion beneath the skin of a patient and extending into a blood vessel, the method comprising steps of:
   a. disposing a patient mounted tubing system comprising a single extension tube in fluid connection with the indwelling portion, the tubing system defining an internal volume and at least one proximal terminal,
   b. flowing flush solution from the external fluid source, through said at least one proximal terminal and through the tubing system into the indwelling portion, at least a portion of the solution at least partially filling the internal volume, promptly sealing the proximal terminal of the tubing system such that at least a portion of the flush solution remains sealed within the tubing system thereby defining a residual volume of flush solution within the tubing system, and
   c. progressively reducing the internal volume of the tubing system to displace at least sequential portions of the residual volume into the indwelling portion to intermittently flush the indwelling catheter portion with the flush solution, wherein the steps of progressively reducing comprises reducing the volume of the single extension tube a first time, to thereby define a first residual volume of the extension tube, and reducing the volume of the single extension tube a second time to thereby define a second residual volume of the extension tube, the second residual volume of the extension tube being less than the first residual volume of the extension tube.

2. A method for intermittently flushing the lumen of an indwelling catheter with flush solution derived from an external fluid source when the catheter is no longer in fluid communication with the external fluid source, the catheter having an indwelling portion defining a lumen beneath the skin of a patient, the lumen extending into a blood vessel and being in fluid connection with the blood vessel, the method comprising steps of:
   a. disposing a single extension tube in fluid connection with the lumen of the indwelling portion of the catheter, the single extension tube system defining an internal volume and at least one proximal terminal,
   b. flowing flush solution from the external fluid source, through at least one terminal and into the extension tube, at least a portion of the solution at least partially filling the extension tube,
   c. sealing the proximal terminal of the extension tube such that at least a portion of the flush solution remains sealed within the extension tube thereby defining a residual volume of flush solution within the extension tube, and
   d. sequentially reducing the internal volume of the extension tube a plurality of different times to displace sequential portions of the residual volume of the flush solution into the lumen to flush the lumen with the flush solution so that patency of the lumen is maintained for an extended period of time, wherein the steps of sequentially reducing comprises reducing the volume of the single extension tube a first time, to thereby define a first residual volume of the extension tube, and without refilling the extension tube, reducing the volume of the single extension tube a second time to thereby define a second residual volume of the extension tube, the second residual volume of the extension tube being less than the first residual volume of the extension tube.

3. A method for intermittently flushing the lumen of an indwelling catheter with flush solution derived from an extension tube in fluid connection with the catheter, the extension tube defining an internal volume and having a sealed proximal terminal, the method comprising steps of:
   a. injecting flush solution into the extension tube through the sealed proximal terminal to define an initial volume of flush solution within the extension tube,
   b. after a first interval of at least several hours, reducing the internal volume of the extension tube a first time to force flush solution distally out of the extension tube and along the lumen, thereby defining a first residual fluid volume of flush solution within the extension tube after the internal volume of the extension tube has been reduced the first time, the first residual fluid volume being less than the initial volume,
   c. after a second interval of at least several hours, again reducing the internal volume of the extension tube a second time to force flush solution distally, out of the extension tube and along the lumen, thereby defining a second residual volume of flush solution within the extension tube after the internal volume has been reduced the second time, the second residual volume being less than the first residual volume,
   d. after a third interval of at least several hours, again reducing the internal volume of the extension tube a third time to force flush solution distally, out of the extension tube and along the lumen, thereby defining a third residual volume of flush solution within the extension tube after the internal volume has been reduced the third time, the third residual volume being less than the second residual volume.

4. The method of claim 3 wherein, reducing the volume of the extension tube a first time comprises compressing the extension tube.

5. The method of claim 3 wherein, reducing the volume of the extension tube a first time, a second time, and a third time comprises compressing the extension tube a first time, a second time, and a third time respectively.

6. A method of maintaining the patency of a lumen of an indwelling catheter over a 24-72 hour period, the lumen being connected with a single fluid locked extension tube filled with flush solution, the extension tube defining an internal volume, the method comprising steps of; sequentially reducing the internal volume of the extension tube a plurality of different times to express sequential portions of the flush solution from the extension tube into the lumen to sequentially flush the lumen at a plurality of different times, wherein the steps of sequentially reducing comprises reducing the volume of the single extension tube a first time, to thereby define a first residual volume of the extension tube, and without refilling the extension tube, reducing the volume of the single extension tube a second time to thereby define a second residual volume of the extension tube, the second residual volume of the extension tube being less than the first residual volume of the extension tube.

7. The method of claim 6 wherein the steps of sequentially reducing the volume of the extension tube comprises sequentially compressing the extension tube.

\* \* \* \* \*